United States Patent [19]

Sawyer

[11] Patent Number: 5,344,425
[45] Date of Patent: Sep. 6, 1994

[54] INTRAVASCULAR STENT AND METHOD FOR CONDITIONING THE SURFACES THEREOF

[75] Inventor: Philip N. Sawyer, Brooklyn, N.Y.

[73] Assignee: Interface Biomedical Laboratories, Corp., Brooklyn, N.Y.

[21] Appl. No.: 832,199

[22] Filed: Feb. 6, 1992

Related U.S. Application Data

[63] Continuation-in-part of Ser. No. 583,882, Sep. 20, 1990, Pat. No. 5,108,417.

[51] Int. Cl.$^5$ .............................................. A61B 17/00
[52] U.S. Cl. ...................................... 606/198; 600/36; 623/1; 623/12; 623/901
[58] Field of Search .................. 606/191, 198; 600/36; 623/901, 1, 12

[56] References Cited

U.S. PATENT DOCUMENTS

| | | | |
|---|---|---|---|
| 3,667,069 | 6/1972 | Blackshear et al. | 3/1 |
| 3,868,956 | 3/1975 | Alfidi et al. | 128/345 |
| 4,011,947 | 3/1977 | Sawyer | 206/363 |
| 4,441,215 | 4/1984 | Kaster | 3/1.4 |
| 4,503,569 | 3/1985 | Dotter | 3/1.4 |
| 4,512,338 | 4/1985 | Balko et al. | 128/1 R |
| 4,553,545 | 11/1985 | Maass et al. | 128/341 |
| 4,560,374 | 12/1985 | Hammerslag | 604/49 |
| 4,580,568 | 4/1986 | Gianturco | 128/345 |
| 4,649,992 | 3/1987 | Wiktor | 128/344 |
| 4,665,918 | 5/1987 | Garza et al. | 128/343 |
| 4,681,110 | 7/1987 | Wiktor | 128/343 |
| 4,690,684 | 9/1987 | McGreevy et al. | 623/12 |
| 4,733,665 | 3/1988 | Palmaz | 128/343 |
| 4,739,762 | 4/1988 | Palmaz | 128/343 |
| 4,753,236 | 6/1988 | Healey | 128/334 R |
| 4,760,849 | 8/1988 | Kropf | 128/341 |
| 4,768,507 | 9/1988 | Fischell et al. | 128/303 |
| 4,770,176 | 9/1988 | McGreevy et al. | 128/334 R |
| 4,795,458 | 1/1989 | Regan | 623/1 |
| 4,800,882 | 1/1989 | Gianturco | 128/343 |
| 4,830,003 | 5/1989 | Wolff et al. | 128/343 |
| 4,878,906 | 11/1989 | Lindemann et al. | 623/1 |
| 4,886,062 | 12/1989 | Wiktor | 128/343 |
| 4,969,458 | 11/1990 | Witkor | 606/194 |
| 4,986,831 | 1/1991 | King et al. | 623/1 |

OTHER PUBLICATIONS

Parra et al., Prosthetic Titanium Urethral Stents,, Urologic Prosthesis, 1991.

Sawyer, The Relationship Between Surface Charge (Potential Characteristics) of the Vascular Interface and Thrombosis, Annal. N.Y. Acad. Sci. pp. 561–583 1983.

Lee et al., Etiology of Thrombus Formation on Prosthetic Metal Heart Valves, J. Thor. Card. Surg. vol. 63, No. 5 pp. 809–819.

Sawyer, Electrode–Biologic Tissue Interreactions at Interfaces–A Review, Biomat. Med. Dev. Att. Org. vol. 12 No. 3-4, pp. 161–196, 1984–1985.

Sawyer et al., The Role of Surface Phenomena in Intravascular Thrombosis, Bib. Anatom. No. 12, pp. 106–119 1973.

Sawyer et al., Electrochemical Precipitator of Blood Cells on Metal Electrodes: An Aid in the Selection of Vascular Prosthesis?, Proc. Nat. Acad. Sci., vol. 53, No. 2, pp. 294–300, Feb., 1985.

Sawyer et al, "Possible Relationship of Ionic Structure of the Blood–Intimal Interface to Intravascular Thrombosis," *Surgery,* vol. 56, No. 4, pp. 846–854 (1964).

(List continued on next page.)

*Primary Examiner*—Michael H. Thaler
*Attorney, Agent, or Firm*—Pennie & Edmonds

[57] ABSTRACT

An anti-turbulent, anti-thrombogenic intravascular stent of a helically shaped titanium or aluminum strip having an airfoil on internal surfaces thereof for increasing blood flow through the stent without creating areas of stagnant or turbulent flow therein. Also, a method for cleaning the stent for optimum performance in the intended application, and the stents which are cleaned by the process, and novel devices for introducing the stents of the invention into the body of a patient.

17 Claims, 6 Drawing Sheets

OTHER PUBLICATIONS

Dotter, "Transluminally Placed Coilspring Endoarterial Tube Grafts," *Investigative Radiology*, vol. 4, p. 329 (1969).

Sugita et al, "Nonsurgical Implantation of a Vascular Ring Prosthesis Using Thermal Shape Memory Ti/Ni Alloy (Nitinol Wire)," Trans. Amer. Soc. Artif. Intern. Organs, vol. 23 pp. 30–34.

Cragg et al, "Nonsurgical Placement of Arterial Endoprosthesis: A New Technique Using Nitinol Wire," *Radiology*, vol. 147, pp. 259–260 (1983).

Sutton et al, "Vascular Stenting in Normal and Atheroschlerotic Rabbits," pp. 667–683 (1989).

Schatz, "A View of Vascular Stents" *Circulation*, vol. 79, No. 2, pp. 445–457 (1989).

Rollins et al, "Self-Expanding Metallic Stents: Preliminary Evaluation in an Atheroscheleratic Model," *Radiology*, vol. 163, pp. 739–742, 1987.

Sutton et al, "Titanium–Nickel Intravascular Endoprosthesis" AJR, vol. 151, pp. 597–601, 1988.

Oku et al, "A Titanium–Nickel Alloy Intravascular Endoprosthesis," Trans. Amer. Soc. Artif. Intern. Organs, vol. 23, pp. 399–403 (1988).

Wright et al, "Percutaneous Endovascular Stents: An Experimental Evaluation," *Radiology*, vol. 156, pp. 69–72 (1985).

Palmaz et al, "Expandable Intraluminal Vascular Graft: A Feasibility Study," *Surgery*, pp. 199–205 (1986).

Cragg et al, "Percutaneous Arterial Grafting," *Radiology*, vol. 150, pp. 45–49 (1984).

Tominaga et al, "Intravascular Endoprostheses," Trans. Amer. Soc. Artif. Intern. Organs, vol. 23, pp. 376–378 (1989).

Sigwart et al, "Intravascular Stents To Prevent Occlusion and Restenosis After Transluminal Angioplasty," N.E. Jour. Med., vol. 316, No. 12, pp. 701–706 (1987).

Maass et al, "Radiological Follow-up of Transluminally Inserted Vascular Endoprostheses: An Experimental Study Using Expanding Spirals," *Radiology*, vol. 152, No. 3, pp. 659–663 (1984).

Sawyer et al, "Long-Term Patency of Solid-Wall Vascular Prostheses," Arch. Surg., vol. 91, pp. 735–742 (1965).

Harshaw et al, "The Ionic Structure Of the Blood Intimal Interface as an Aid in the Development of Vascular Prostheses," Trans. Amer. Soc. Artif. Organs, vol. 9, pp. 317–320 (1963).

Sawyer et al, "Ionic Architecture at the Vascular Wall Interface," Trans. Amer. Soc. Artif. Organs, vol. 10, pp. 316–319 (1964).

Sawyer et al, "Irreversible Electrochemical Precipitation of Mammalian Platelets and Intravascular Thrombosis," Pro. Nat. Acad. Sci., vol. 53, No. 1, pp. 200–207 (1965).

Wu et al, "Effect of Various Metal Electrode Sutures in the Production of Increased Tensile Strength of Wounds," *Surgical Forum*, vol. 16, pp. 89–91 (1965).

Sawyer et al, "Electrochemical Criteria in the Choice of Materials Used in Vascular Prosthesis," Biophysical Mechanics in Vascular Homeostasis and Intravascular Thrombosis (P. N. Sawyer, editor) Appleton-Century-Crofts, N.Y., N.Y. pp. 337–348, 1967.

Wu et al, "The use of Various Metal Sutures to Increase Tensile Strength of Wounds," *Surgery*, vol. 61, No. 2, pp. 242–247, 1987.

Sawyer et al, "Electrochemical Precipitation of Blood Cells on Metal Electrodes: an Aid in the Selection of Vascular Prostheses?" Proceedings of the National Academy of Sciences, vol. 53, No. 2, pp. 194–300, 1965.

Boddy et al, "Some Electrochemical Properties of Solid–Liquid interfaces and the Electrode Behavior or Erythrocytes, Biophysical Mechanics in Vascular Homeostasis and Intravascular Thrombosis" (P. N. Sawyer, editor) Appleton-Century-Crofts, N.Y., N.Y., pp. 30–41, 1967.

Chopra et al, "Relation between Thrombosis on Metal Electrodes and the position of Metal in Electromotive Series," *Nature*, vol. 215, No. 5109, p. 1494, Sep. 1967.

Wu et al, "Effect of Aluminum Suture on Wound Healing: Long Term comparative Study on the Tensile Strength and Hydroxyproline Content." *Surgery*, vol. 64, No. 3, pp. 605–609, 1968.

Lucas et al, "Nonthrombogenic AC Polarized Copper Prosthesis," *Biomat. med. Der. Art. Org.*, vol. 3, No. 2, pp. 215–232 (1975).

Srinivasan et al., "Thrombosis on Metal Surfaces–Relationship to Position of Metal in the Electromative Series and Metal Blood Interface Potential," *The Physiologist*, vol. 10, No. 3, Aug. 1967.

Sawyer et al, "Electrical Potential Differences Across the Normal Aorta and Aortic Grafts of Dogs" Amer. J. Physiol. 175:113, 1953.

Sawyer et al, "Bioelectric Phenomena as an Etiologic Factor in Intravascular Thrombosis," Surg., 34:491, 1953.

(List continued on next page.)

OTHER PUBLICATIONS

Sawyer et al, "The Experimental Use of Oriented Electric Fields to Delay and Prevent Intravascular Thrombosis," Surg. Forum, Amer. Col. Surg. Forum, Amer. Col. Surg., W. B. Saunders, Phila., 6:173, 1955.

Sawyer et al, "Application of Gas Endarterectomy to Atherosclerotic Peripheral Vessels and Coronary Arteries: Clinical and Experimental Results," Circulation, Suppl. 1,35,36:I–163, 1967.

Dotter et al, "Transluminal Iliac artery Dilatation. Nonsurgical Treatment of Atheromatous Narrowing," JAMA, 230, 117-24, 1974.

Gruentzig et al, "Current Status of Dilatation Catheter and Guiding Systems," Amer. J. Cardiology, 53:92–93C, 1984.

Sawyer et al, "Characteristics of the Human Heart: Design Requirements for Replacement," Trans. ASAIO, 17:470, 1971.

Sawyer et al, "Significance of Electrochemical Phenomena in Intravascular Thrombosis," Nature, 206:1162, 1965.

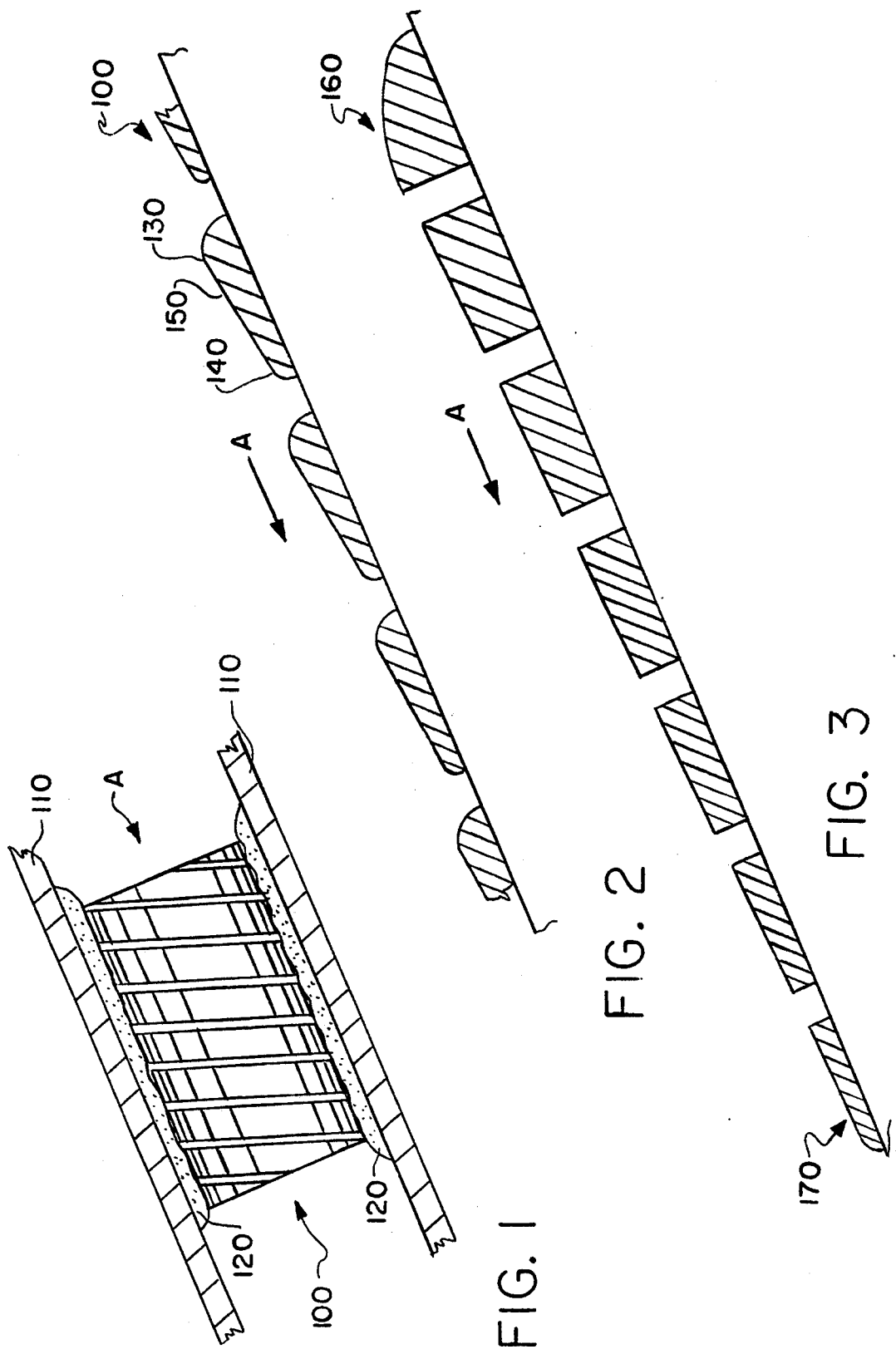

INTRAVASCULAR STENT AND METHOD FOR CONDITIONING THE SURFACES THEREOF

CROSS-REFERENCE TO RELATED APPLICATIONS

This application is a continuation-in-part of U.S. patent application Ser. No. 07/583,882, filed Nov. 20, 1990, now U.S. Pat. No. 5,108,417.

FIELD OF THE INVENTION

This invention relates to an intravascular stent to maintain vascular patency in humans and animals. Also, the invention relates to a means for reducing the risk of thrombosis due to the implanted stent.

BACKGROUND OF THE INVENTION

Intravascular stents have long been applied to maintain vascular patency. Intravascular stents are used in conjunction with balloon angioplasty wherein a balloon is inflated to expand a constricted vessel in order to restore proper blood flow. The intravascular stent is then positioned inside the now expanded vessel to ensure the vessel maintains the enlarged diameter.

However, attempts to develop a prosthetic stent which would hold open a blood vessel and not develop transluminal thrombus have enjoyed limited long term success. There has been very little significant improvement with the exception of an effort to create a more expansible metallic stent.

For a metallic stent to satisfy the limits for antithrombogenesis while simultaneously maintaining the lumen of a blood vessel in which the stent has been placed, the stent has to fulfill the electrochemical laws for thrombosis. That is, the stent has to maintain a potential difference more negative than plus 250 millivolts versus the normal hydrogen electrode. In addition, the stent must exhibit limited corrosion and limited tissue destruction over the duration of the stent life. It was found very early on that while some of the metals on the corrosive side of the electromotive series would maintain a very negative potential, many of these metals upon ionizing and going into solution produced cellular destruction due to tissue and cellular toxicity. For this reason, the number of materials which can be used to develop a metallic implantable intravascular stent is limited to four or five metals that are known to be anti-thrombogenic and anti-corrosive. The most useful of these appears to be titanium and aluminum.

Titanium and aluminum produce a non-soluble surface oxide on exposure to blood and tend not to go into solution. In addition, titanium and aluminum develop a very negative potential with reference to the normal hydrogen electrode. Titanium and aluminum deposit almost no coagulant materials, coagulant enzymes, or proteins.

A number of patents have been found describing various stent designs as well as methods for delivery of the stent to the desired position in the vessel. These patents include:

U.S. Pat. Nos. 3,868,956 and 4,503,569, each of which describes methods wherein a stent comprising a temperature responsive device is implanted in the damaged vessel and thereafter expanded by means of an external heat source.

U.S. Pat. No. 4,553,545, which discloses a method whereby a complex mechanical rotating device and coaxial cables are employed to increase the diameter of the implanted stent.

U.S. Pat. No. 4,580,568, which describes a stent wherein a single wire forming a closed loop is expanded in the damaged vessel to maintain vascular patency. The loop of wire is compressed to form a series of straight segments and bends, wherein the bends store energy in the compressed state. Upon removal of a compression means the stent expands and exhibits a circular configuration.

U.S. Pat. No. 4,649,992, which describes a device in combination with a catheter which is a compression spring retained by a partially inflated balloon and an abutment immediately behind the balloon on the catheter shaft. The spring prosthesis is transported in this manner to the desired location and released by totally evacuating the balloon thereby allowing the spring prosthesis to expand linearly.

U.S. Pat. No. 4,681,110, which describes a catheter for delivery of a stent comprising woven plastic strands forming a tube which can be compressed radially. The orientation of the plastic strands provide the resilience for tube to expand from the compressed state.

U.S. Pat. No. 4,768,507, which discloses a catheter comprising an outer cylinder and inner core, wherein said inner core comprises spiral grooves for containing a coil spring stent. Pliers are used to facilitate the loading of the coil spring into said grooves whereupon completion of the loading of the outer cylinder is placed over the inner core thereby retaining the coil in they compressed state until the coil is released.

U.S. Pat. Nos. 4,690,684, and 4,720,176, each of which discloses a stent for aligning the ends of the vessel during anastomosis by thermal bonding. The stent comprises an integral solid of biologically compatible material to align the vessel ends together during anastomosis. Upon completion of the anastomosis the stent fully melts into the fluid flowing through the vessel. U.S. Pat. No. 4,770,176 also discloses a method of anastomosing a vessel utilizing the stent described in U.S. Pat. No. 4,690,684.

U.S. Pat. No. 4,878,906, which describes a prosthesis comprising a flexible thin-walled plastic sleeve for repairing damaged vessels. The sleeve having sufficient length to cover the damages area of the vessel forms a sealed interface on its outer peripheral ends with the inner peripheral surface of the vessel, thereby providing a bridge, bypassing the damaged area of the vessel.

U.S. Pat. No. 4,830,003, which discloses a cylindrical shaped stent comprising angled wires of biocompatible metal. The angled wires are connected obliquely at alternate ends to form a compressible open ended tube.

U.S. Pat. No. 4,866,062, which discloses a radially expandable coronary stent. The stent comprises a flat expandable wire band which is preformed in a zigzag pattern to provide expansion capability. The band which is wound into a cylindrical shape is inflated by means of a variable diameter device. The band expands radially exhibiting a cylindrical shape with increasing diameter.

U.S. Pat. Nos. 4,800,882, 4,739,762 and 4,733,665, each of which discloses an expandable intraluminal graft. These grafts are made of wire or a thin walled tubular member and can be expanded by an angioplasty balloon associated with a catheter.

U.S. Pat. No. 4,760,849, which discloses a planar blank which may be made into a helical coil spring stent.

U.S. Pat. No. 4,665,918, which describes a system and method for implanting a generally tubular prosthesis member having an unobstructed central passageway into the length of a blood vessel. The prosthesis member contracts to a smaller dimension for delivery through the unobstructed portion of the blood vessel, and is outwardly expansible in the blood vessel. The prosthesis member is positioned in a contracted condition between a delivery catheter and outer sheath, and expands outwardly in response to the removal of the sheath.

None of the aforementioned patents, however, disclose an anti-thrombogenic stent which decreases turbulence and improves hydraulic flow of blood therethrough. Accordingly, there remains a need for such a device.

SUMMARY OF THE INVENTION

It is an object of the present invention to provide an improved intravascular stent, whereby the intravascular stent decreases the turbulence and improves the hydraulic flow of the blood through the vessel, thus, reducing the possibility of transluminal or "out flow turbulence" thrombus developing in conjunction with the implanted stent.

Another object of the present invention is to provide an intravascular stent that satisfies the electrochemical laws for thrombosis while exhibiting limited corrosion over the duration of stent life.

The improvements of this invention over the prior art devices are the ability of the present invention to decrease the turbulence of blood flow and to improve the hydraulic flow of the blood through the vessel.

These improvements are achieved in an anti-turbulent, anti-thrombogenic intravascular stent comprising a helically shaped strip of predetermined thickness of a non-thrombogenic material capable of assuming a contracted position for insertion into a blood vessel and expansible to a normally expanded position having a first end, a second end, an outer surface in contact with the blood vessel for urging the blood vessel outwardly, and an internal surface in contact with blood passing therethrough from the first end to the second end. The stent internal surface includes an airfoil for increasing the rate of blood flow through the stent without creating areas of stagnant or turbulent flow therein or adjacent thereto.

A preferred material for the stent is titanium or aluminum and an airfoil may be formed on the strip of non-thrombogenic material by including a leading edge and a trailing edge connected by a smooth transition area therebetween across the width of the strip, with the height of the leading edge being greater than that of the trailing edge. Alternatively, the airfoil can be formed by providing the predetermined thickness of the strip at the first end to be greater than the predetermined thickness of the strip at the second end, with the predetermined thickness of the strip between the first and second ends gradually diminishing to form a relatively smooth transition therebetween. Furthermore, the airfoil can be formed by configuring the stent to have a relatively narrower internal diameter near the first end and a relatively larger internal diameter near the second end.

The invention also relates to a process for preparing a stent by conditioning the surfaces thereof prior to introduction of the stent into the body of a subject. This process includes the steps of forming a stent in a desired size and configuration, removing dirt and organic material from the surfaces of the stent, pickling the surface of the stent with an oxidizing compound to provide a relatively uniform oxide layer thereon, polishing the surfaces of the stent, removing oxides from the surfaces of the stent and retaining the stent in a substantially oxygen free environment until use thereof.

The dirt and organic substances are removed from the surfaces of the stent by immersing the stent into a detergent solution, preferably of a concentrated liquid detergent, with the stent generally being immersed into the detergent solution after formation. It is also possible to clean the stent material prior to forming the stent.

The pickling step comprises immersion of the cleaned stent into a concentrated oxidizing acid, such as nitric acid, hydrofluoric acid or mixtures thereof. This provides a uniform oxide layer on the surface of the stent.

The surface polishing step can be an electrochemical cleaning of the surfaces of the stent in a basic solution, such as concentrated sodium hydroxide. In addition, the stent can be electrically connected to a source of electrons to cathodically clean the surfaces thereof. Preferably, the stent is electrically connected to the negative pole of a battery while immersed in the basic solution with an anode of a noble metal such as platinum which is electrically connected to the positive pole of the battery.

Following the polishing step, oxides may be removed from the surfaces of the stent by immersion into an acidic solution of a concentrated inorganic acid such as, e.g., hydrochloric acid. Thereafter the stent is retained in a solution of substantially oxygen free distilled water or in the presence of an inert gas until it is to be implanted into the subject.

The present invention also provides novel devices for introducing these stents into the body of a patient. These devices include a first generally tubular member having proximal and distal ends and a stent receiving channel of a diameter which is smaller than the free diameter of a stent which is to be received thereby, This channel is preferably located near the distal end of the tubular member. Also, a flexible cover member is used to retain the stent in a contracted position in the stent receiving channel. This cover member is movable from a first position where the flexible cover member retains the stent in the channel and a second position where the flexible cover member is retracted away from the distal end of the tubular member to allow the stent to attempt to achieve its free diameter and exit the channel. The device further includes means for moving the flexible cover member between the first and second positions, with the moving means being located near the distal end of the first tubular member.

The cover member preferably comprises a second generally tubular member which is slideably engaged with the outer diameter of the first tubular member, and the moving means preferably comprises a first finger member connected to the first tubular member, a second finger member spaced apart from the first finger member and connected to the second tubular member, and means for aligning the first and second finger members. Thus, in this arrangement, as the finger members are brought toward each other, the second tubular member is moved toward said second position. Also, the device can include a first balloon member in a deflated condition and positioned at least partially within the stent receiving channel to assist the stent to achieve its free diameter by inflating the first balloon member after the cover means is retracted.

The device may also have a distal tip assembly which is configured and dimensioned to facilitate introduction of the device into the body of a patient. This distal tip assembly can be made of a solid material in the shape of a bullet, or a second balloon member located near the distal end of the first tubular member for fixing the position of the distal end of the device in the body of the patient by inflation of the second balloon member, and means for supporting position detection means at said distal tip of the device. The position detection means comprises an ultrasonic scanning member, and the tip assembly may further comprise means for directing laser energy to the distal end of the device.

An enclosure surrounding at least the distal end of the device and including a substantially oxygen free medium therein may be included to prevent oxidation of the stent prior to use thereof. This enclosure preferably includes a tab member for removal to gain access into the enclosure, and the enclosure may substantially surround the entire device.

The present invention also relates to the above described device in combination with a stent located in the stent receiving channel. Yet another aspect of the invention relates to a method of introducing the stent into a body of a patient through the use of one of the above described devices.

BRIEF DESCRIPTION OF THE DRAWINGS

FIG. 1 is a side view of a stent in accordance with the present invention in position in a blood vessel;

FIG. 2 is an exploded view of the stent of FIG. 1 to show the airfoil surface thereof;

FIG. 3 is an exploded view of another airfoil surface for a stent according to the invention;

DETAILED DESCRIPTION OF THE INVENTION

Figure 5:
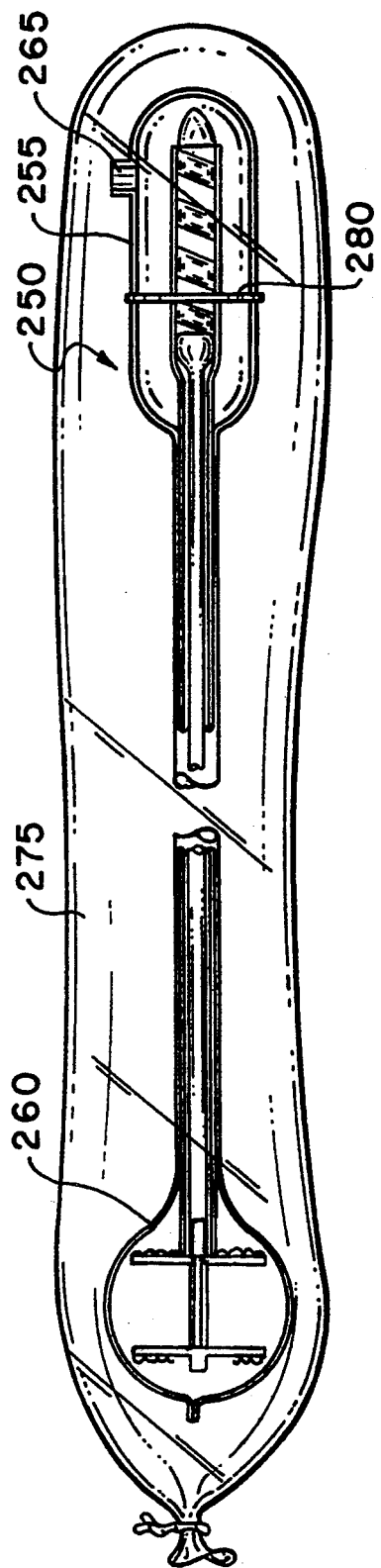
FIG. 5 is a perspective view of a stent introducer which is packaged for delivery to an operating location.

The stent of the present invention is preferably a titanium or aluminum air foil helix. FIG. 1 illustrates that stent 100 in position in a blood vessel 110. When implanted onto an obstruction 120 in the vessel 110, the outer surface of the stent 100 contacts the obstruction and inner surface of the vessel. The inner surface of the stent 100 allows blood to flow therethrough. Advantageously, the inner surface of the stent is shaped in the form of an airfoil. These shapes can be made by machining a flat strip of titanium or aluminum followed by configuring the machined strip in the form of a helix. The airfoil surface is achieved by configuring each stent segment to mimic the configuration of an airplane wing. Thus, each segment has a leading edge 130 of greater height than trailing edge 140, with a smooth transition 150 therebetween, as shown in FIG. 2. Thus, the thickness and cross sectional area of the stent is uniform throughout its length.

FIG. 3 illustrates an alternate embodiment of an airfoil surface for the stent of the invention. In this embodiment, the thickness of the strip at the forward end 160 of the stent is made thicker than that of the rearward end 170 of the stent. The thickness of the strip between the forward and rearward ends gradually diminishes to form a relatively smooth transition area. Thus, the overall configuration of the internal surface of the stent is similar to that of an airplane wing. The spaces between the surface segments formed by the strip do not detract from its utility of increasing blood flow without creating turbulence of stagnant areas.

As the fluid in the vessel passes over the stent, the airfoil configuration increases the velocity of the blood flow therethrough in the same manner as air flows over the wing of an airplane. Blood flows in the direction of arrow A from the forward end to the rearward end of the stent. The increased velocity of the blood flow passing through said stent reduces the possibility of thrombosis because the blood flows more rapidly past the area which previously experienced the buildup or obstruction.

When a blood vessel has an obstruction, blood also flows faster as it passes the obstruction, but it produces turbulence and stagnant pools of blood distal to the obstruction. This can cause thrombus and blood element growth of the obstruction due to material depositing from the turbulent and stagnant blood pools. The present invention avoids these problems by configuring the inner portion of the stent to have an airfoil or venturi, tube like surface. Thus, as blood flows by, its speed is increased and its pressure is decreased without creating turbulent or stagnant areas of blood. This higher speed, lower pressure blood flow moves rapidly past the stent, thus preventing the deposition of material therefrom. Also, the lower pressure of the blood flowing through the stent causes any material which would tend to deposit to be pulled away from the wall of the vessel where the stent is located. By use of the stent of the invention, the obstruction is removed and means are provided to prevent its regrowth.

Advantageously, the stent is formed from a thrombosis resistant material, such as titanium or aluminum, as noted above. The titanium or aluminum stent upon exposure to blood maintains a potential difference more negative than 250 millivolts versus the normal hydrogen electrode, thereby fulfilling the electrochemical laws for prevention of thrombosis. Also, titanium and aluminum stents exposed to blood deposit almost no coagulant materials, coagulant enzymes or proteins, thereby further reducing the possibility of thrombosis. In addition, metals which tend to go into solution produce cellular destruction due to tissue and cellular toxicity thereby reducing stent life. Stents of titanium, and to a slightly lesser degree aluminum, produce a non-soluble oxide on exposure to blood and tend not to go into solution, thus preventing a shortened stent life.

To provide the optimum surface condition of the stent to prevent or resist the formation of thrombus, the stent may be cleaned by a particular preparation process. This process provides a non-soluble oxide of a uniform thickness on the exposed surfaces of the stent, and this enables the stent to provide an optimum useful service life after insertion into the body environment.

Pure titanium has been found to be the most preferred material for the stents of the invention. It is generally utilized at a thickness of abut 2 to 5 mils to produce a helical strip of the desired diameter and having 15 to 20 coils. As noted above, the inner surface of this stent would form an airfoil by either of the procedures described above (i.e., stent configuration or strip thickness).

The specific preparation process is as follows:

1) A helical coil stent of pure titanium is produced from a specified form, such as a wire or flat strip, and in a predetermined configuration, such as a straight coil of uniform diameter, a variable diameter coil, or a coil having an airfoil on its internal surfaces.

2) The coil is washed and degreased in a concentrated cationic detergent, such as Wisk ® liquid detergent, to remove any organic or inorganic foreign matter from the stent.

3) The coil is then pickled by immersion into a solution of an oxidizing acid, such as a mixture of 96% nitric acid and 4% hydrofluoric acid to provide a substantially uniform oxide layer on the surfaces of the stent.

4) The stent is then cathodically cleaned in a concentrated sodium hydroxide solution by connecting the stent to the negative pole of a suitable battery of 9 to 27 volts, connecting a platinum electrode to the positive pole of the battery, and immersing the stent and platinum electrode in the sodium hydroxide solution for about 2 to 10 seconds to debur and polish the stent.

5) The stent is then rinsed with distilled water by spraying the stent with the water or immersing the stent into the distilled water.

6) The stent is then treated by immersion into concentrated hydrochloric acid (preferably 5M or greater) for about 2 to 3 minutes to remove substantially all oxides from the exposed surfaces of the stent.

7) The stent is then rinsed with oxygen free water one to three times by spraying the stent with the water or immersing the stent into the water.

8) Finally, the stent is stored in distilled oxygen free water in a sealed container until ready for implantation into a patient. Instead of distilled oxygen free water, the stent can be packaged under nitrogen (or other inert gas) until use.

Stents cleaned and prepared according to the previously described method provides a number of unexpected advantages during use in the intended application in the body. When utilized as an intravascular stent, for example, the stents of the invention exhibit essentially no corrosion to the body environment, cause essentially no tissue or inflammatory response with no measurable detrimental effect on blood chemistry or platelets.

Figure 4:
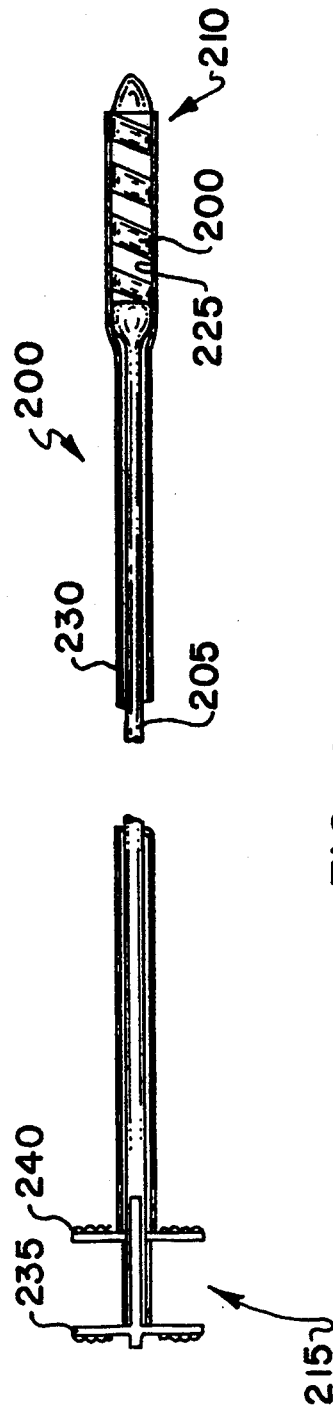
FIG. 4 is a perspective view of a stent introducer.

The stent of this invention can also be inserted and be transported via certain novel delivery systems. One such system is illustrated in FIG. 4. The introducer 200 includes a first tubular member 205 having a distal end 210 and a proximal end 215. As shown in the FIG., stent 220, which may be any of the coil stents described herein, is contracted to a smaller diameter than its free diameter, and is placed into the stent receiving channel 225 which is located near the distal end 210 of the device. The term "free diameter" is used to mean the normal diameter which the stent will assume in the absence of constriction or expansion forces thereon. One skilled in the art knows that the stent is made to have a free diameter which is substantially the same or slightly larger than the diameter of the blood vessel or other body cavity into which the stent is to be inserted. Thus, in the introducer of the present invention, the stent 220 is contracted to a diameter which is smaller than its free diameter, and it is retained in this state in the channel 225 by a second flexible tubular member 230. The first 205 and second 230 tubular members may be made of a thermoplastic material which has low friction properties and sufficient strength and rigidity to pass through the blood vessels of the patient. The second member 230 is generally made of a more flexible material compared to that of the first member 205 so that it can be easily retracted slideably along the outer diameter of the first tubular member 205.

At the proximal end 215 of the device 200 are found the first and second finger members 235, 240, which are connected respectively to the first and second tubular members 205, 230. When the second tubular member 230 is positioned over the stent 220, the first and second finger members are spaced apart as shown in the FIG. To release the stent 220 from the introducer, the first and second finger members are grasped by the surgeon, and are moved toward each other. This causes the second tubular member to be retracted from the distal end 210 of the device. As soon as the second tubular member 230 clears the proximal end of the stent 220, the stent can attempt to expand to its free diameter and exit the channel 225 to engage the inner diameter of the blood vessel.

In order to retain a surface conditioned stent in the desired condition prior to use, the stent must be maintained in a substantially oxygen free environment, such as under an inert gas atmosphere or immersed in oxygen free distilled water. FIG. 5 illustrates as enclosure 250 which can be utilized to maintain the stent in this state. Enclosure 250 includes a bubble chamber 255 which surrounds the stent and stent receiving channel, and a envelope 260 which passes around the remainder of the device 200. This envelope is substantially identical to that disclosed in U.S. Pat. Nos. 4,011,947 and 4,065,816, the content of each of which is expressly incorporated by reference herein. The bubble chamber 255 includes gas or water injection port 265 which has a soft elastomer plug therein to facilitate the introduction of the desired oxygen free environment around the stent. After the desired environment is achieved about the stent and introducer, the enclosure 250 is sealed within a plastic bag 275 or other suitable storage device until needed by the surgeon. At that time, the plastic bag 275 is opened and access to the introducer is made by removing tear tab 280 from the bubble chamber. Thereafter, the distal tip 210 of the device may be inserted into the patient and the stent released therefrom after the device is properly positioned.

Figure 6:
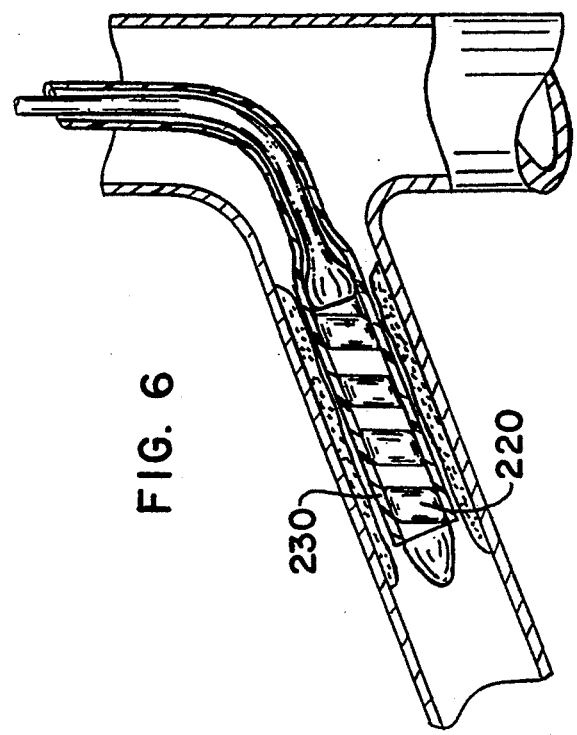
FIG. 6 is a view in cross-section of the use of the introducer of FIG. 4 to implant the stent into a blood vessel.
Figure 7:
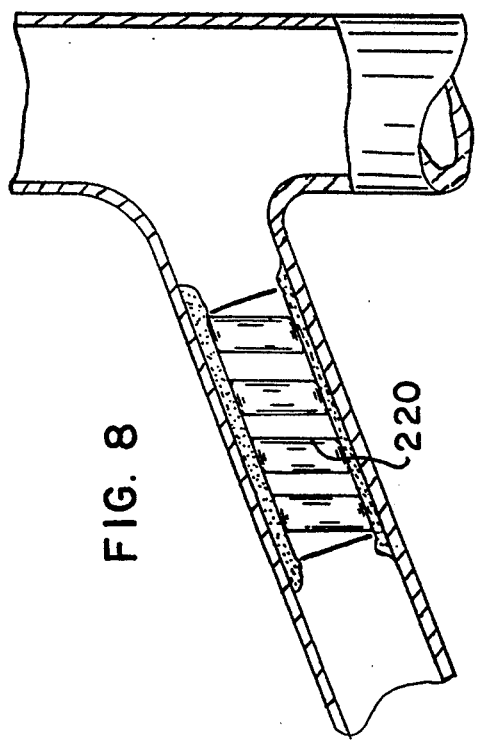
FIG. 7 is a view in cross-section of the introducer in place in the blood vessel immediately after releasing the stent therein.
Figure 8:
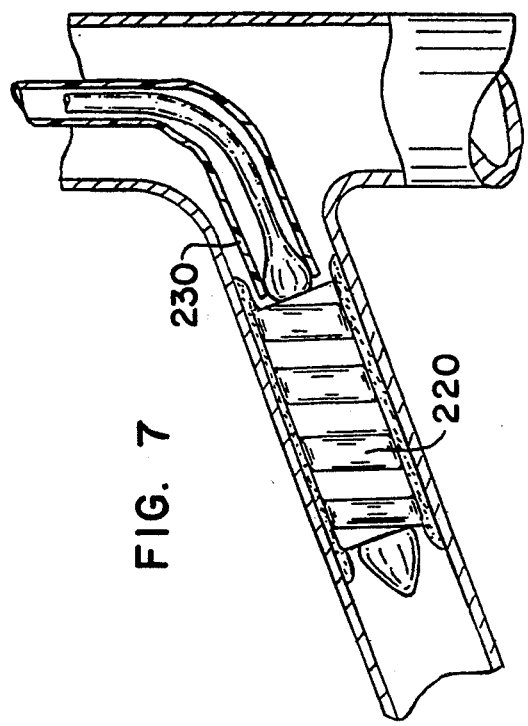
FIG. 8 is a view in cross-section of the blood vessel having the stent placed therein.

FIGS. 6-8 illustrate the insertion of the introducer into the blood vessel of a patient. Upon reaching the desired location in the damaged blood vessel, the second tubular member 230 of the delivery system is removed as described above. FIG. 6 shows the device prior to removal of tubular member 230, while FIG. 7 shows the tubular member 230 retracted and the stent 220 expanded radially to contact the inner walls of the blood vessel thereby preventing an decrease in the diameter of the vessel. FIG. 8 illustrates the stent 220 in position in the blood vessel after removal of the introducer.

Figure 9:
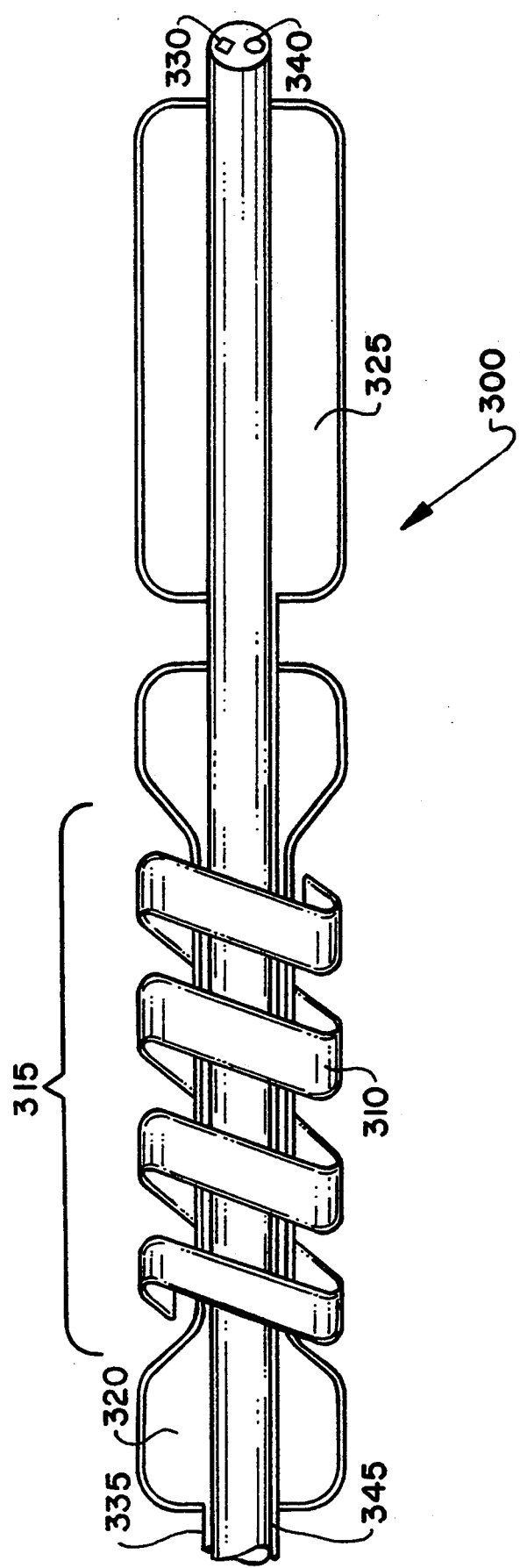
FIG. 9 is a perspective view of another introducer for the stents of the invention.

FIG. 9 illustrates another introducer 300 for the stents of the present invention. In this embodiment, only the distal tip is different in that a special assembly is utilized. The proximal end, the second tubular member moving means, and the enclosure described above with respect to FIGS. 4 and 5 would be the same for introducer 300.

FIG. 9 illustrates the distal tip of the introducer 300 with the second tubular member in its retracted position and immediately before the expansion of the stent 310 to its free diameter. In this embodiment, the stent receiving channel 315 is formed by a first balloon member 320 which is partially deflated. If desired, the first balloon member can be partially located beneath the stent 310. As the stent 310 attempts to achieve to its free diameter, the surgeon can assure that the stent completely expands by inflating balloon member 320. This is advantageous for the situation where the blockage of the blood vessel has not been completely cleared or removed, since the balloon 320, when inflated, will open the blood vessel and force the stent to achieve its free diameter against the inner diameter of the blood vessel.

To assure proper placement of the stent 320 into the blood vessel, the tip assembly of this embodiment includes a second balloon member 325 mounted on the distal end of the device. This balloon can be utilized in a variety of ways. First, it can be used to open a partially blocked vessel prior to the introduction of the stent therein. Also, balloon member 325 can be inflated to fix the position of the distal tip of the device in the blood vessel to control the position of the stent 315 and to resist movement of the position of the stent as the second tubular member is being retracted. In addition, the device can include an ultrasonic scanner 330 to assist in the determination of the position of the distal tip of the device in the blood vessel. If desired, an optical fiber 340 can be included in the device, for viewing the position of the distal end thereof or for directing laser energy to the distal end of the device to cause ablation of obstructions in the blood vessel. Both scanner 330 and optical fiber 340 would extend through the first tubular member back to the proximal end of the device where the appropriate connections can be made. Also, the first and second balloon members 320, 325 are inflated by a suitable inflating medium, such as saline or water, through conduits 335, 345 respectively, which extend to the proximal end of the device. After completion of the placement of the stent, the balloon members are deflated and the introducer device can be withdrawn.

Figure 10:
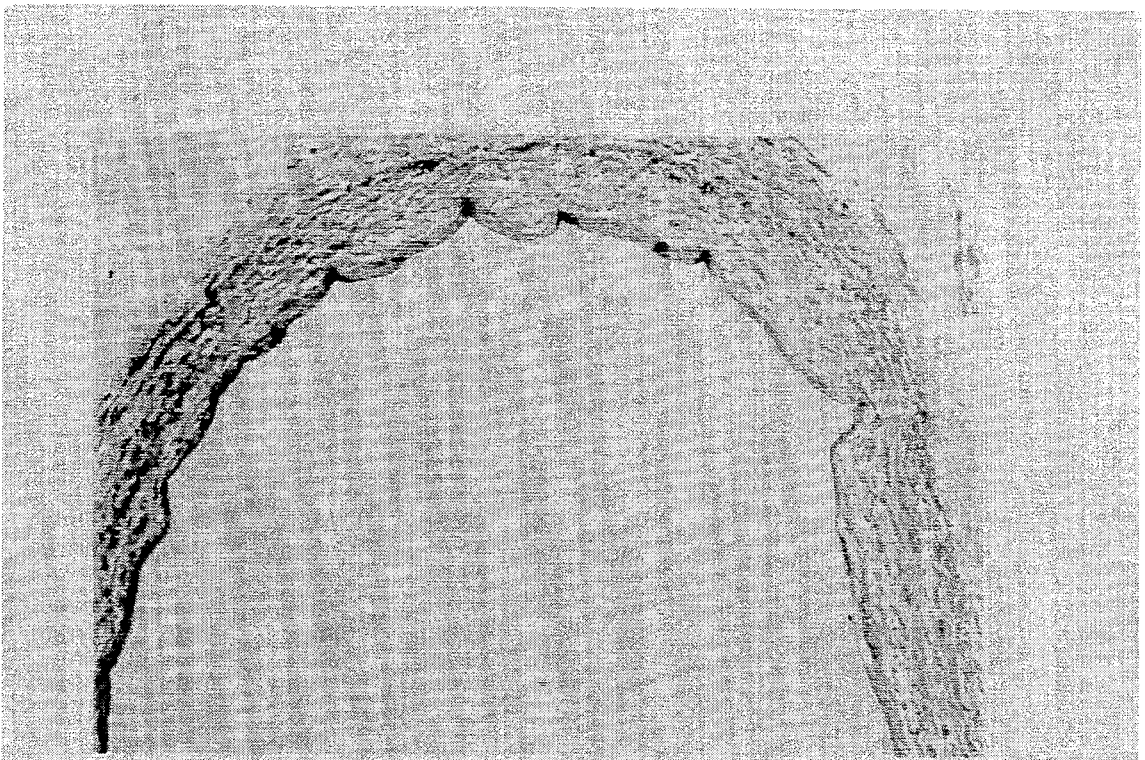
FIGS. 10–12 are photomicrographs of in vivo performance for the stents of the present invention.
Figure 11:
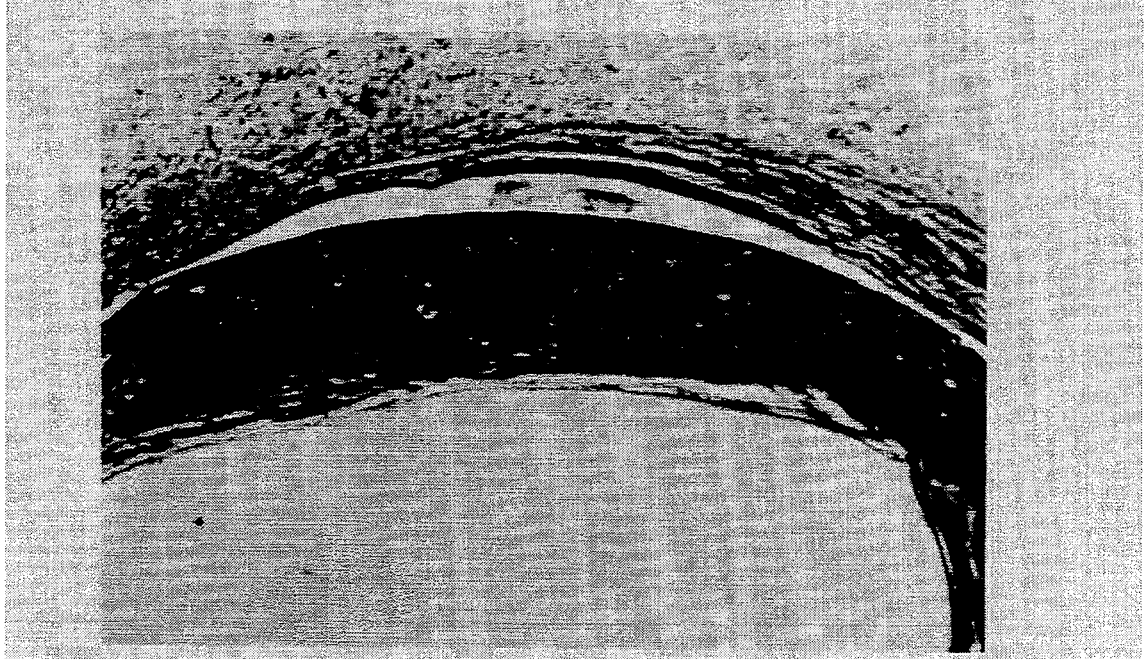
Figure 12:
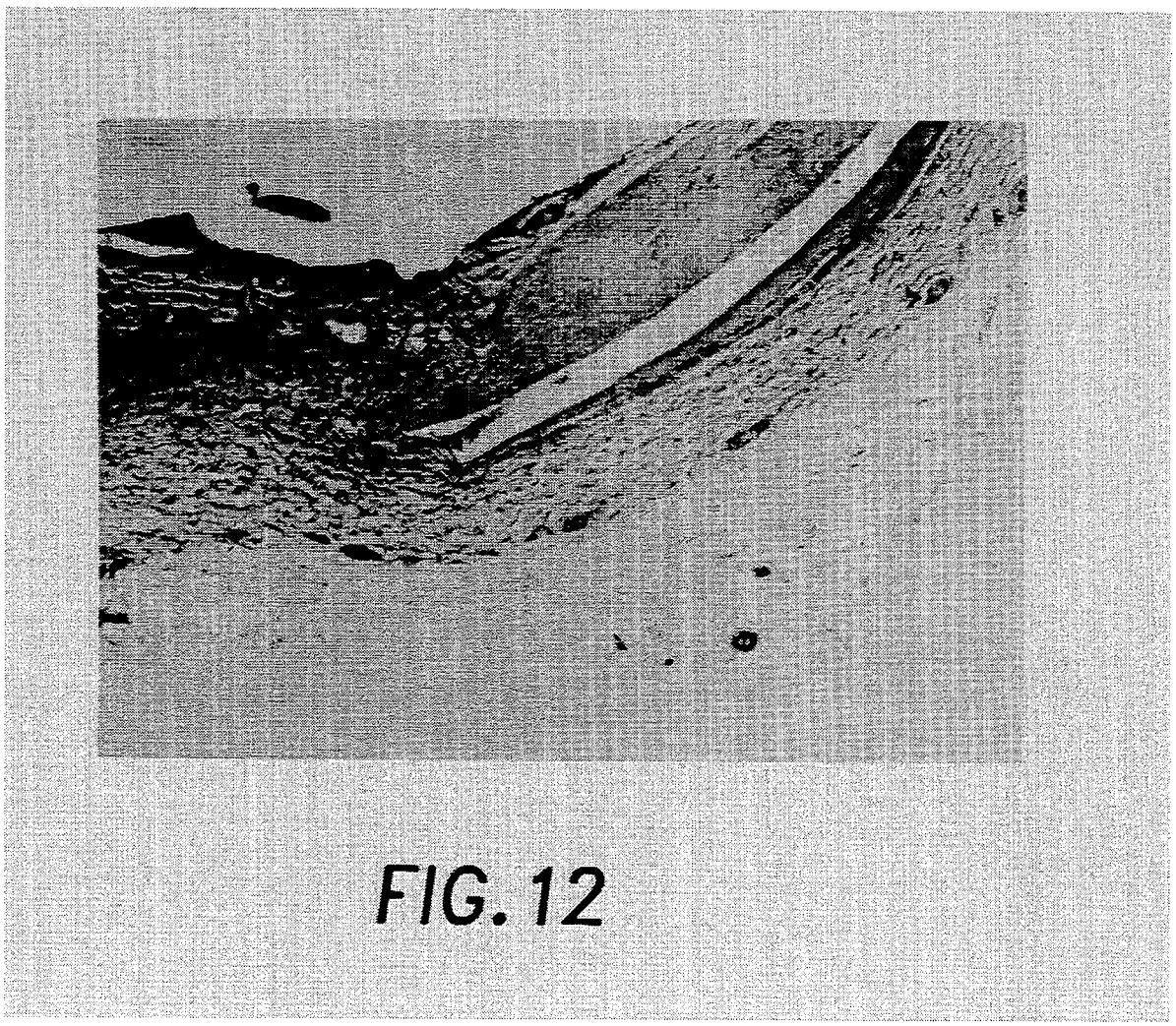

FIGS. 10–12 are photomicrographs of in vivo performance for the stents of the present invention. FIG. 10 illustrates a stent prepared as described above after 8 months implantation in the right jugular vein of a dog. No anticoagulant was used either before, during or after implantation. The photomicrograph shows that the vein is intact, there is no evidence of thrombus formation, no inflammatory response and no karyolysis.

FIG. 11 illustrates a second section of the vein of FIG. 10. The open space which is visible delineates the wall of the jugular vein from the inner fibrous capsule. In this FIG., the results are essentially the same as in FIG. 10, except that the was an inner fibrous capsule of a thickness of up to about 100 microns. Again, the architecture of the vein is intact.

FIG. 12 illustrates a section of the left jugular vein of a dog which had implanted a stent according to the present invention after eight months. The groove which presented when the stent was removed is clearly visible. In this FIG., the results are essentially the same as in FIG. 11. Again, the histology and architecture of the tissues which rested against the stent appear to be normal and unaffected.

While it is apparent that the invention herein disclosed is well calculated to fulfill the objects above stated, it will be appreciated that numerous modifications end embodiments may be devised by those skilled in the art. For example, the internal surface airfoil configuration may be obtained by bending or cold forming a strip, rather than by machining such surfaces on the strip. It is intended that the appended claims cover all such modifications and embodiments as fall within the true spirit and scope of the present invention.

What is claimed is:

1. A method for preparing a titanium stent by conditioning the surfaces thereof prior to introduction into the body of a subject, which comprises:
   forming a stent by cutting or machining a titanium strip to a desired size and configuration;
   cleaning the surfaces of the stent to remove dirt and organic material therefrom;
   pickling the cleaned stent with an oxidizing acid to provide a substantially uniform oxide layer thereon;
   electrochemically polishing the surfaces of the pickled stent;
   removing oxides from the surfaces of the stent after the polishing step by treatment with an acidic solution; and
   retaining the stent in a substantially oxygen free environment after the oxide-removing step until use thereof.

2. The method of claim 1 wherein the pickling step comprises treating the surfaces of the stent with nitric acid, hydrofluoric acid, or mixtures thereof.

3. The method of claim 3 wherein the oxides are removed from the surfaces of the stent by immersing the stent into an acidic solution.

4. The method of claim 3 wherein the acidic solution comprises a concentrated inorganic acid, and the oxide removing step is conducted after the polishing step.

5. The method of claim 2 wherein the stent is retained in a solution of substantially oxygen free distilled water or in the presence of an inert gas.

6. The method of claim 1 wherein the dirt and organic substances are removed from the surfaces of the stent by immersing the stent into a detergent solution.

7. The method of claim 6 which further comprises washing the stent after detergent cleaning and thereafter subjecting the washed stent to the surface polishing step wherein the stent is electrochemically cleaned in a basic solution.

8. The method of claim 7 which further comprises washing the electrochemically cleaned stent and thereafter subjecting the cleaned stent to the oxide removal step wherein the stent is immersed into an acidic solution.

9. The method of claim 8 which further comprises washing the stent after immersion into the acidic solution with a first solution of substantially oxygen free distilled water prior to retaining the stent in a second solution of substantially oxygen free distilled water or in the presence of an inert gas.

10. The method of claim 14 which further comprises forming the stent of titanium; selecting the basic solution to include concentrated sodium hydroxide; selecting the electrochemically cleaning step to include electrically connecting the stent to a source of electrons to cathodically clean the surfaces thereof; and selecting the acid solution to be concentrated hydrochloric acid.

11. The method of claim 6 which further comprises selecting the oxidizing acid for the pickling step to be a strong inorganic acid.

12. The method of claim 11 wherein the detergent solution comprises a concentrated liquid detergent, and the stent is immersed into the concentrated liquid detergent after formation.

13. The method of claim 11 wherein the electrochemical polishing step comprises electrochemically cleaning the surfaces of the stent in a basic solution with the stent electrically connected to a source of electrons.

14. The method of claim 13 wherein the stent is electrically connected to the negative pole of a battery and is immersed into the basic solution with an anode of a noble metal that is electrically connected to the positive pole of the battery.

15. The method of claim 13 wherein the oxides are removed from the surfaces of the stent by immersing the stent into an acidic solution.

16. The method of claim 15 which further comprises washing the stent between one or more of the surface conditioning steps.

17. A cleaned and conditioned stent prepared according to the method of claim 1.

* * * * *